United States Patent
Tayebi

(10) Patent No.: US 9,056,144 B1
(45) Date of Patent: Jun. 16, 2015

(54) NON-CLOGGING, NON-DRIPPING AND SPILLAGE AND LEAKAGE-PROOF AIR-SCENTING METHOD AND DEVICE

(76) Inventor: Amad Tayebi, Westford, MA (US)

( * ) Notice: Subject to any disclaimer, the term of this patent is extended or adjusted under 35 U.S.C. 154(b) by 537 days.

(21) Appl. No.: 13/506,532

(22) Filed: Apr. 25, 2012

Related U.S. Application Data

(63) Continuation-in-part of application No. 12/930,588, filed on Jan. 11, 2011, now Pat. No. 8,517,283, which is a continuation-in-part of application No. 12/928,372, filed on Dec. 11, 2010, now Pat. No. 8,464,965, and a continuation-in-part of application No. 12/462,367, filed on Aug. 1, 2009, now Pat. No. 8,276,830, application No. 13/506,532, which is a continuation-in-part of application No. 12/657,382, filed on Jan. 20, 2010, now abandoned.

(60) Provisional application No. 61/188,858, filed on Aug. 13, 2008, provisional application No. 61/630,783, filed on Dec. 19, 2011, provisional application No. 61/571,257, filed on Jun. 23, 2011, provisional application No. 61/519,497, filed on May 23, 2011, provisional application No. 61/518,741, filed on May 11, 2011, provisional application No. 61/517,747, filed on Apr. 25, 2011.

(51) Int. Cl.
*A24F 25/00* (2006.01)
*A61L 9/03* (2006.01)
*A61L 9/12* (2006.01)

(52) U.S. Cl.
CPC .. *A61L 9/037* (2013.01); *A61L 9/12* (2013.01)

(58) Field of Classification Search
CPC .............. A61L 9/037; A61L 9/12; A61L 9/14
USPC ...................... 239/47, 51.5, 53, 55, 42, 57, 58
See application file for complete search history.

(56) References Cited

U.S. PATENT DOCUMENTS

| | | | | |
|---|---|---|---|---|
| 4,214,038 A * | 7/1980 | McCarty et al. | ............... | 427/242 |
| 5,230,867 A * | 7/1993 | Kunze et al. | ................... | 422/123 |
| 5,383,598 A * | 1/1995 | Styles | ............................... | 239/57 |
| 5,395,047 A * | 3/1995 | Pendergrass, Jr. | ............... | 239/56 |
| 5,422,078 A * | 6/1995 | Colon | ........................... | 422/123 |
| 5,782,409 A * | 7/1998 | Paul | ............................... | 239/56 |
| 6,938,832 B2 * | 9/2005 | Sada | ............................... | 239/41 |

\* cited by examiner

*Primary Examiner* — Davis Hwu
(74) *Attorney, Agent, or Firm* — Amad Tayebi; American Patent Associates

(57) ABSTRACT

A non-clogging, non-dripping and spillage and leakage-proof air-scenting device is disclosed in which a flat bonded porous fibrous mass is impregnated with a mass of air-scenting liquid not exceeding the dripping liquid mass of the extent of the bonded fibrous mass. The surface segments of the fibrous mass have at least one of i) higher capillary pressure, ii) higher mass density, and iii) lower average fiber denier than the interior body of the fibrous mass. The bonded fibrous mass is enclosed between two impermeable membranes sealed around their perimeter and having an opening covered with a removable impermeable liner.

1 Claim, 8 Drawing Sheets

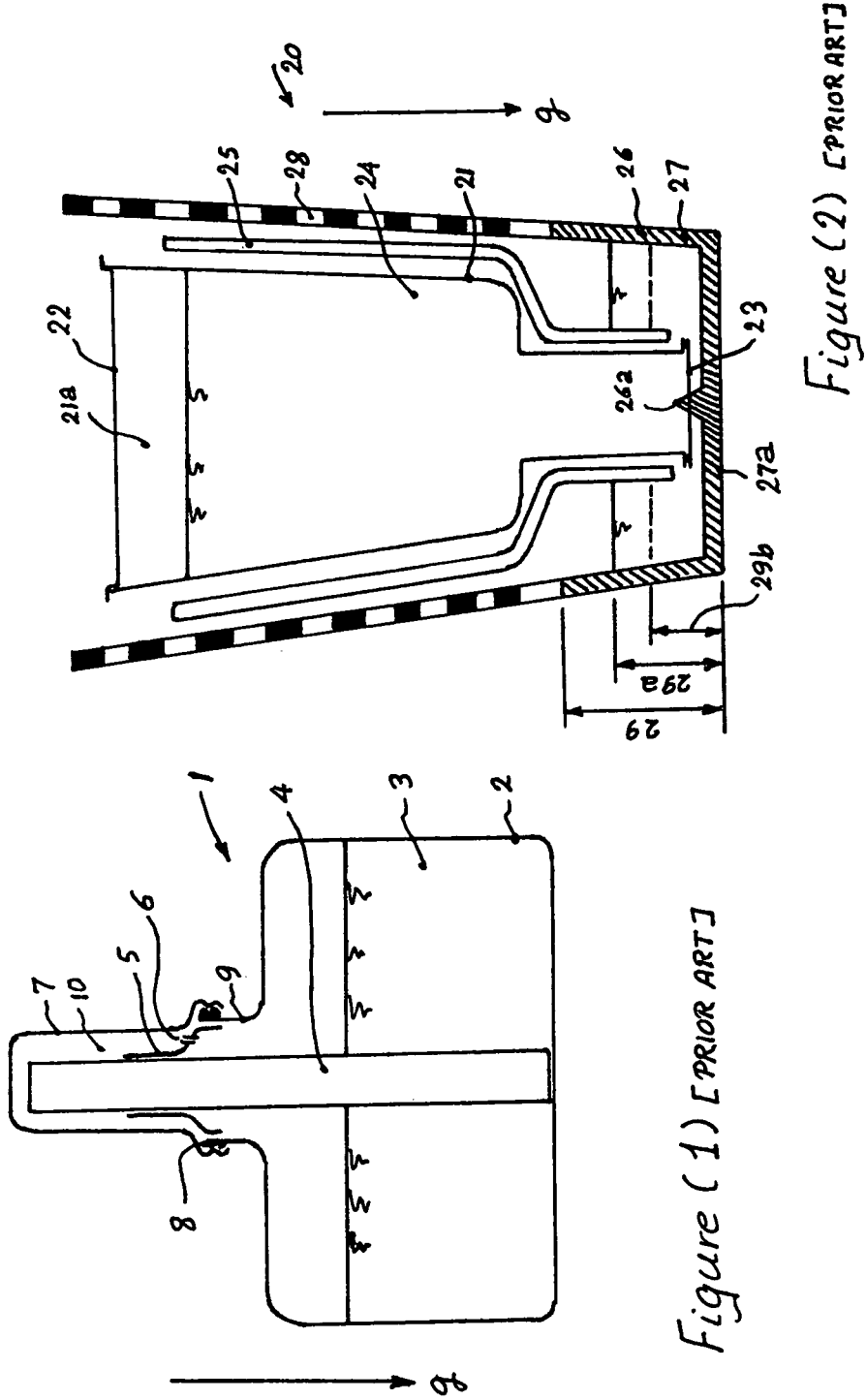

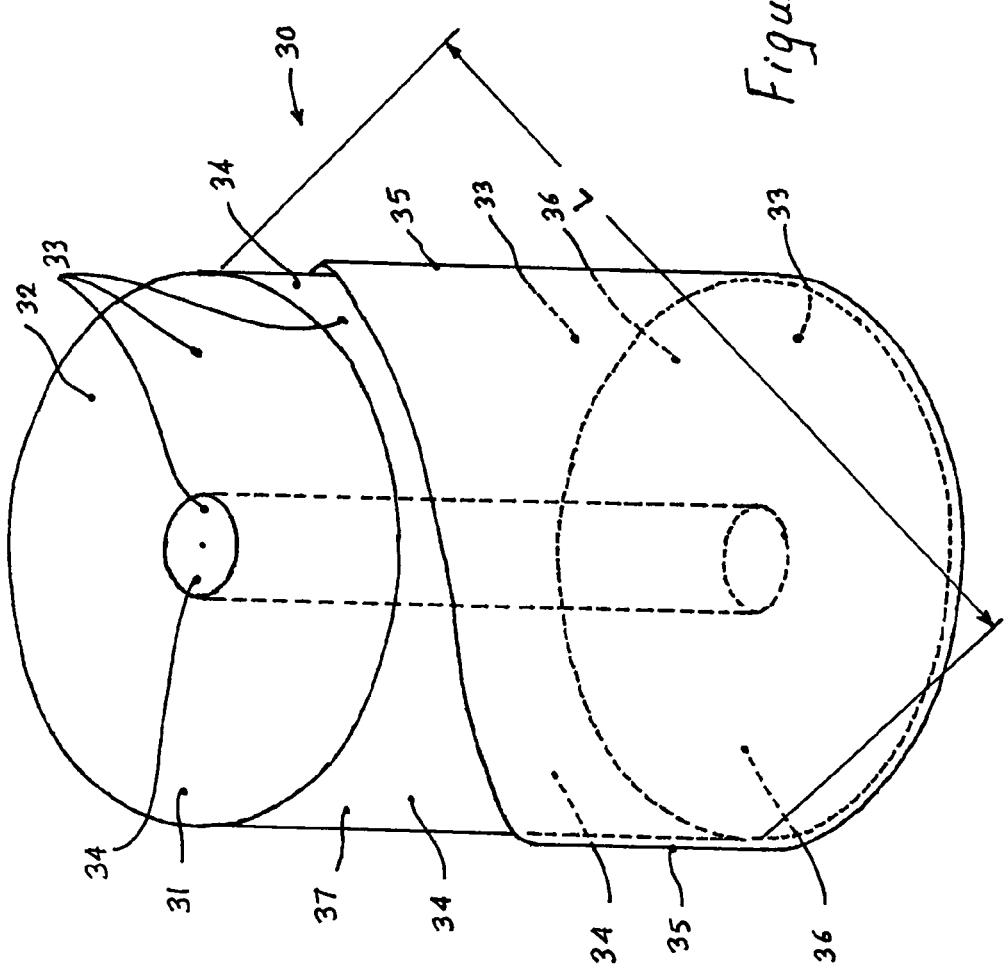

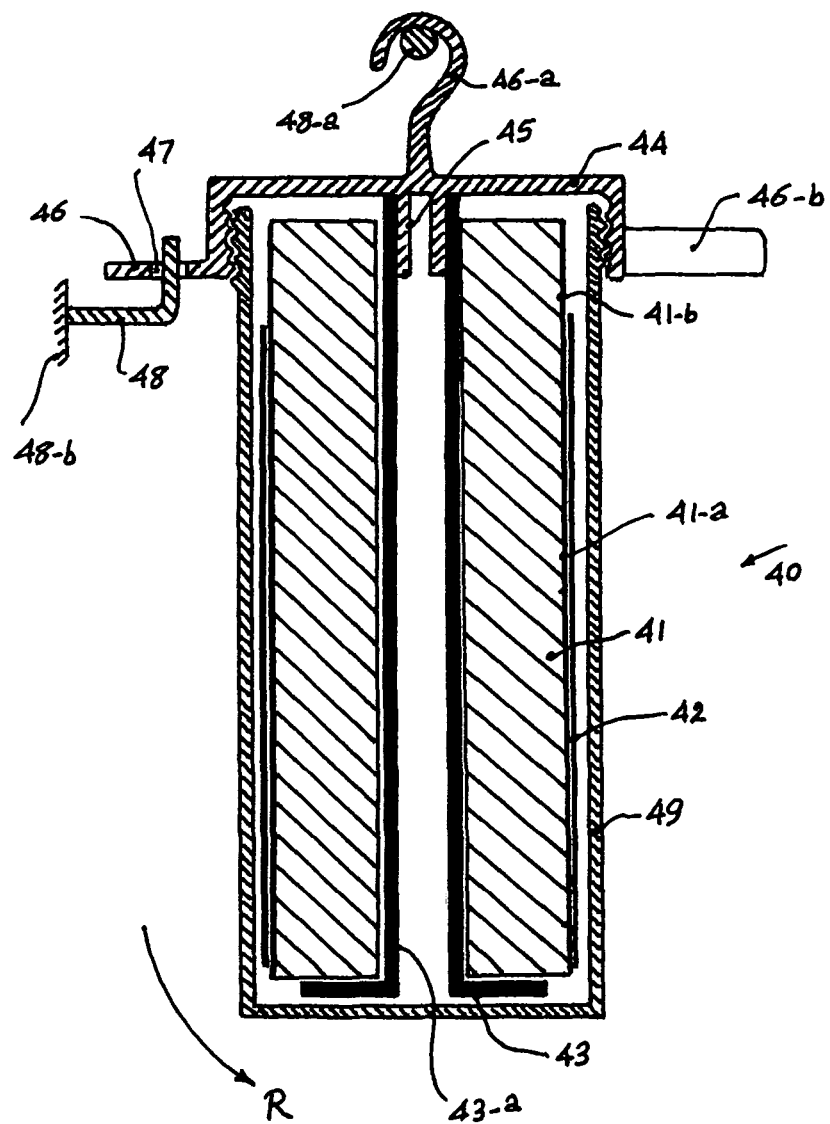
Figure (4)

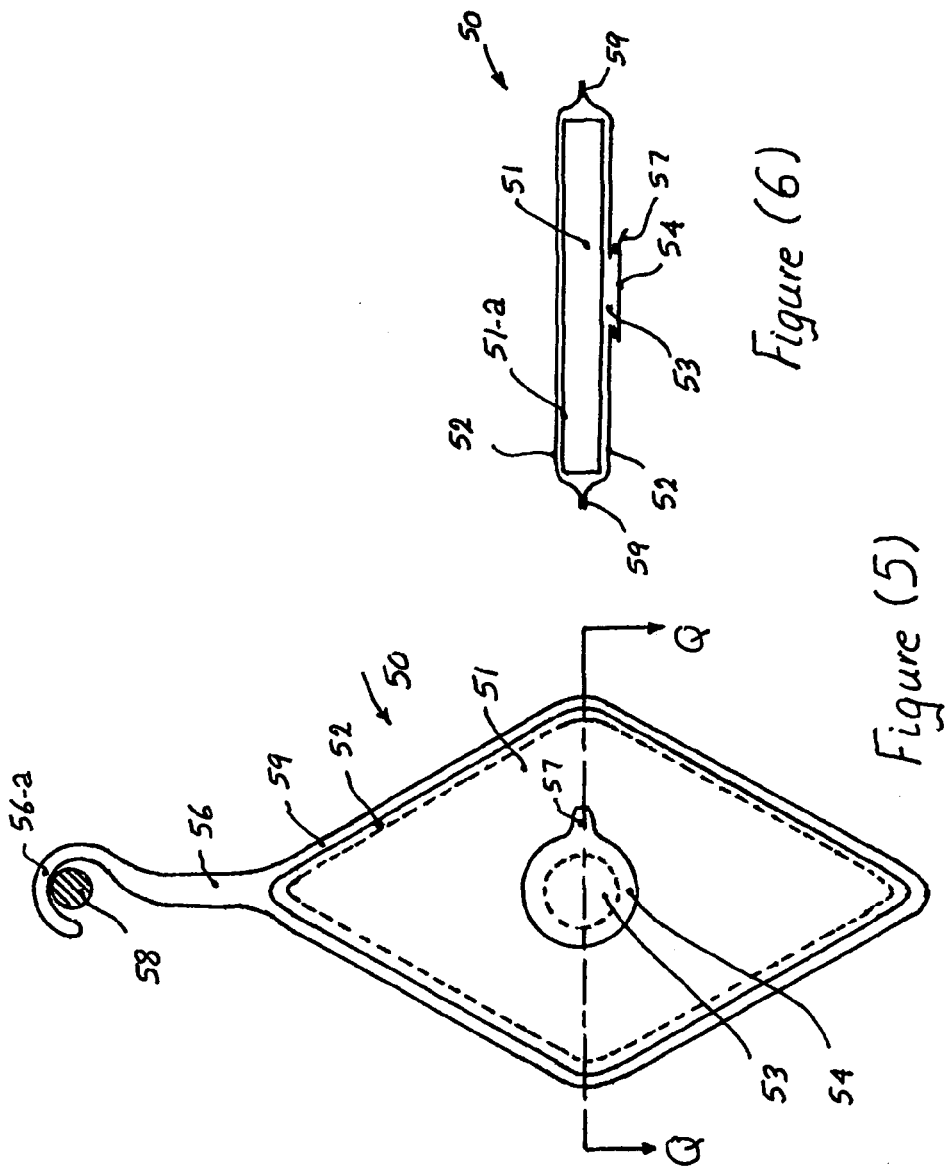

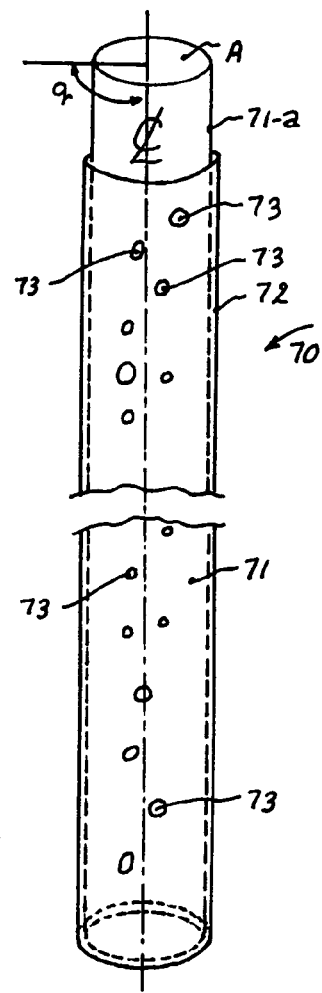
Figure (7)
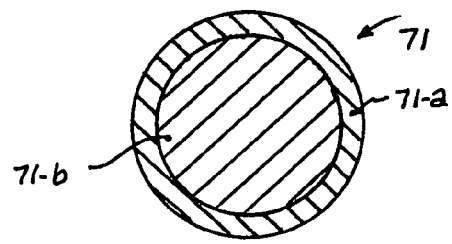
Figure (8)
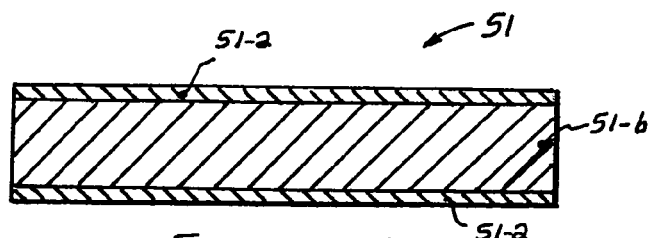
Figure (9)

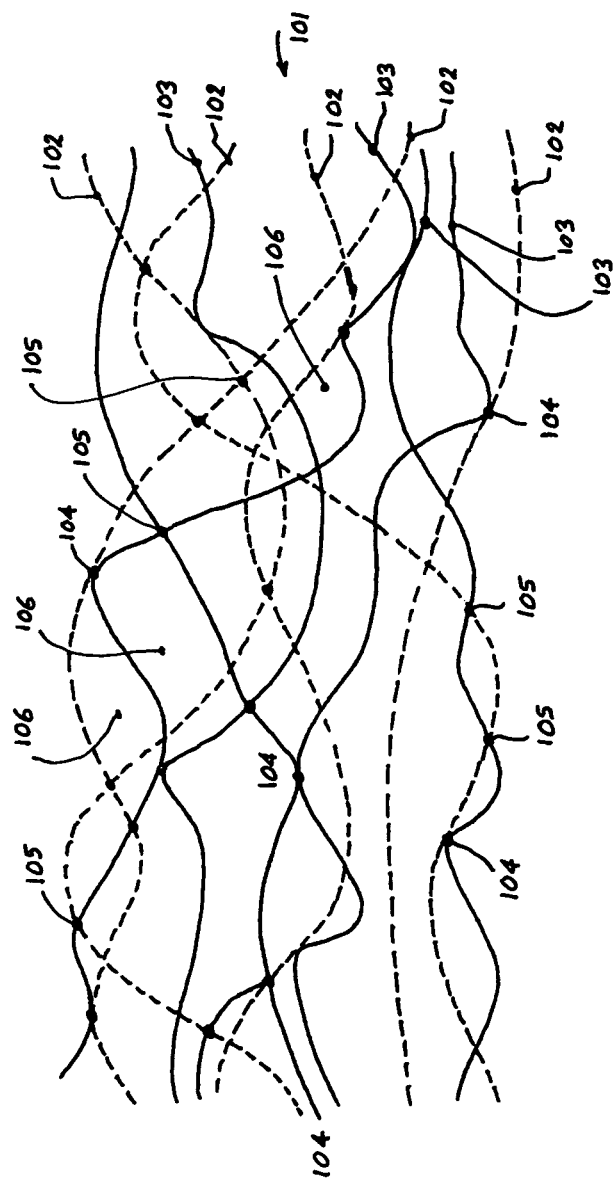
Figure (10)

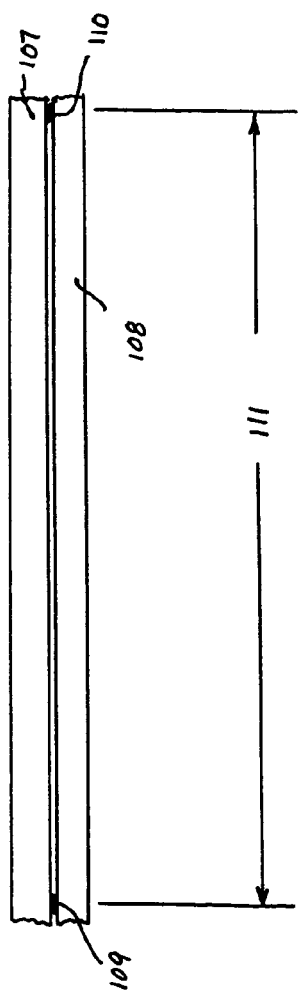
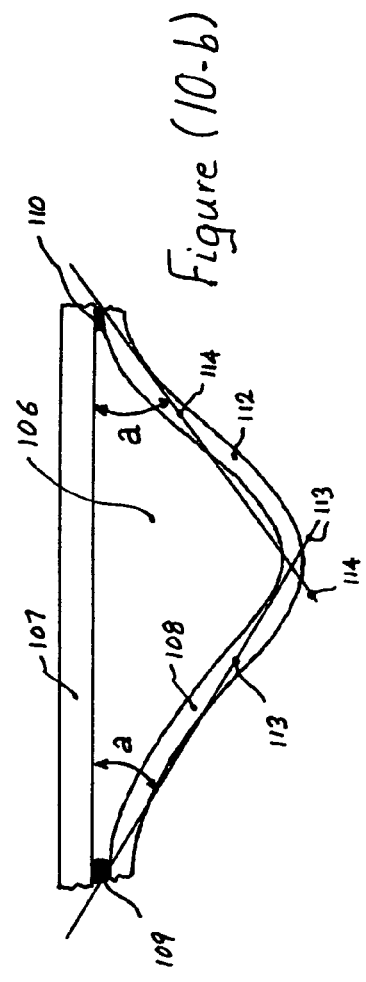

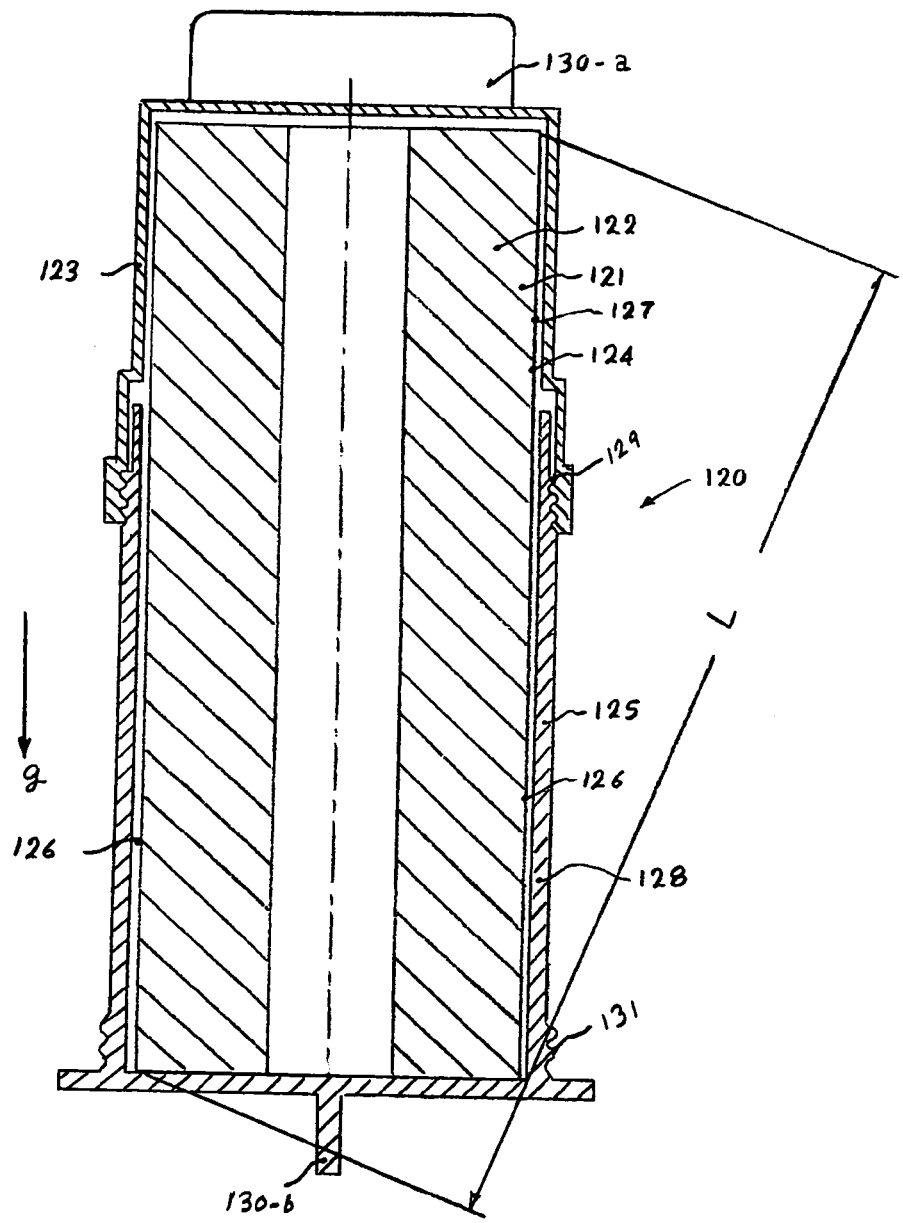
Figure (11)

NON-CLOGGING, NON-DRIPPING AND SPILLAGE AND LEAKAGE-PROOF AIR-SCENTING METHOD AND DEVICE

This Continuation in Part utility patent application claims priority of and is a Continuation in Part of a related Continuation in Part utility patent application filed on Jan. 11, 2011 (Ser. No. 12/930,588), titled "Non-Clogging, Non-Dripping and Spillage and Leakage—Proof Air-Scenting Method and Device" now issued as U.S. Pat. No. 8,517,283. Continuation in Part utility patent application, Ser. No. 12/930,588, claims priority of and is a Continuation in Part of a related Continuation in Part utility patent application filed on Dec. 11, 2010 now U.S. Pat. No. 8,464,965 (Ser. No. 12/928,372), titled "Non-Dripping and Spillage and Leakage-Proof Air-Scenting Method and Device".

Continuation in Part utility patent application (Ser. No. 12/928,372, Dec. 11, 2010) claims priority of and is a Continuation in Part of a related utility patent application filed on Aug. 1, 2009 now U.S. Pat. No. 8,276,830, Ser. No. 12/462,367, titled "Child-Resistant Air-Scenting Device) and submitted by the same applicant. Utility patent application 12/462,367 claims priority of Provisional patent application filed on Aug. 13, 2008, Ser. No. 61/188,858 titled "Apparatus and Method for Scenting Air" and submitted by the same applicant. As such, this Continuation in Part utility patent application also claims priority of provisional patent application Ser. No. 61/188,858 and incorporates, by reference and in their entireties, each of Ser. No. 12/462,367 and Ser. No. 61/188,858 applications.

This Continuation in Part utility patent application also claims priority of a related utility patent application (Ser. No. 12/657,382, Filing Date: Jan. 20, 2010) now abandoned and incorporates by reference and in its entirety said Ser. No. 12/657,382 application.

This Continuation in Part utility patent application also claims priority of each of Provisional Patent applications (61/517,747 [Apr. 25, 2011], 61/518,741 [May 11, 2011], 61/519,497 [May 23, 2011], 61/571,257 [Jun. 23, 2011] and 61/630,783 [Dec. 19, 2011]) and incorporates by reference and in their entireties each of said Provisional Patent applications.

FIELD OF AND AN OVERVIEW OF THE INVENTION

The present invention is in the field of air scenting methods and devices for commercial, industrial and home applications. In particular, it is directed to a non-clogging, non-dripping and spillage and leakage-proof air-scenting method and device which are achieved by making, providing and using a resilient porous bonded fibrous foam/mass having open pores/open cells formed between bonded fibers with different stress-free thermal shrinkages and eliminating the presence of any free-to-flow air-scenting liquid mass in the device. In accordance with the present invention, the air-scenting liquid mass is contained/retained substantially entirely within the open pores/cells of the porous bonded fibrous mass. The fibrous mass has a body B and an exterior surface S. Body B has a capillary pressure BCP, a mass density MDB (gram per cubic centimeter), an average fiber denier FDB, and a fiber orientation index FOIB relative to an axis or a direction. The exterior surface S comprises surface segments SG. Surface segments SG have at least one of i) a capillary pressure SCP, where SCP is higher than said capillary pressure BCP, ii) a mass density of MDSG (gram/cubic centimeter) where MDSG is higher than said mass density MDB, iii) an average fiber denier FDSG where FDSG is lower than said FDB, iv) fiber orientation/alignment index FOISG where FOISG is higher than said FOIB as measured relative to said axis or direction, and v) a surfactant coating applied to said surface segments.

In accordance with the present invention, a method of making a non-clogging resilient porous bonded fibrous foam or mass comprises the steps of:

1) providing an intimately-blended fibrous mass, said fibrous mass comprising a first group of staple fibers and a second group of staple fibers, said first group of staple fibers and said second group of staple fibers being non-absorbent of and non-reactive with (i.e., inert to) the liquid to be wicked by and evaporated through the surface of the formed non-clogging resilient porous bonded fibrous foam/mass or to be held within the open pores/open cells of said foam/mass, said first group of staple fibers having i) a percent weight W1 (%) of weight of said fibrous mass, ii) an average fiber denier D1, iii) a ratio N1 where N1 is equal to W1/D1, iv) a staple length L1, in the range of 1.5 to 3.5 inches, v) a tack point T1 and vi) a percentage longitudinal stress-free shrinkage S1 (%) at said tack point T1, said second group of staple fibers having i) a percent weight W2 (%) of weight of said fibrous mass, ii) an average fiber denier D2, iii) a ratio N2 where N2 is equal to W2/D2, iv) a staple length L2, in the range of 1.5 to 3.5 inches, v) a tack point T2, where T2 is higher than T1 by at least 50 degrees Fahrenheit, vi) a percentage longitudinal stress-free shrinkage S2 (%) at said tack point T1, and a ratio R equal to N1/N2 and being within the range of 0.5 to 3.0, and preferably within the range of 1.0 to 2.25 and a percentage longitudinal stress-free shrinkage difference SD (%) equal to the absolute (positive) value of the difference between S1 (%) and S2 (%) and being at least equal to 5.0%, 2) heating said fibrous mass to a temperature of at least T1 but lower than T2 by feeding said fibrous mass into a heat bonding (cohesive bonding) die, said bonding die having a feed/inlet zone, a heating zone, a tapered compaction zone and a shaping/cross-section-forming zone for making/shaping the final cross sectional shape of the bonded fibrous mass. The heating zone of said die is fed with hot steam or hot air at a temperature of at least T1 but lower than T2. The compaction zone is preferably tapered, towards the delivery/exit end of the die, at an angle within the range of 10 degrees to 45 degrees and preferably within the range of 25 degrees to 35 degrees, per side, relative to the axis of the die in order to provide more effective contact and higher heat transfer contact time and rate from the die body to the fibrous mass surface/surface segments thus effecting a calendaring or glazing action that renders the exterior surface/surface segments, of the bonded fibrous mass, having higher capillary rise and/or a higher density than the interior of the bonded fibrous mass, 3) Pulling the fibrous mass through said die thus dragging the fibrous mass, through the tapered compaction zone of the die, against the interior surface of the die and causing the fibers on the exterior surface of the bonded fibrous mass to have a higher fiber orientation index, relative to the direction of the axis of the die, than the fibers contained within the interior of the bonded fibrous mass, and 4) Cutting the bonded fibrous mass to a desired length.

In embodiments, in accordance with the present invention, the intimately blended fibrous mass may be in the form of slivers, yarns (single and/or plied yarns), braided yarns, woven fabrics, knitted fabrics (tubular or flat) or needle punched nonwoven sheets which may also be arranged in layers which may be parallel flat layers or concentric circular layers/annular rings having outer layer(s) made of finer fibers (lower denier). The heating zone of the die is fed and filled with hot steam or hot air at a temperature of approximately 10 to 20 degrees Fahrenheit above T1 thus cohesively bonding fibers of the intimately blended fibrous mass at common contact and cross-over points and causing bonded fibers to form open cells with aspect angle (a), shown in FIG. 10-b, of at least 18 degrees.

FIG. 10 shows a representation of the non-clogging bonded fibrous foam/mass of the present invention. As shown therein, bonded fibrous foam/mass 101 is an intimately-blended fibrous mass comprising a first group of staple fibers 102, shown in solid lines, and a second group of staple fibers 103, shown in dashed lines. Fibers from the first group and from the second group are intimately blended and bonded at common contact points 104 and cross-over points 105. Open pores/cells 106 are formed between the fibers upon heating the intimately blended fibrous mass, bonding fibers at points 104 and 105 and allowing the difference in longitudinal stress-free shrinkage to cause the fibers with the lower longitudinal stress-free shrinkage to buckle and form open pores/cells throughout the bonded porous fibrous mass. The size and dimensions of open pores/open cells 106 depend on the dry mass density of the bonded fibrous foam/mass and on the difference between the percentage longitudinal stress-free shrinkages of the first group of fibers and of the second group of fibers.

To illustrate how open pores/cells 106 are formed, FIG. 10-a shows two fibers, initially straight and of equal length, fiber 107 and fiber 108, bonded together at points 109 and 110. The initial distance between bonding points 109 and 110 is, as shown in FIG. 10-a, distance 111. For the case where, upon heating the bonded together fibers 107 and 108 to a temperature where the percentage longitudinal stress-free shrinkage of fiber 107 is higher than the percentage longitudinal stress-free shrinkage of fiber 108 by only 5%, the bonded assembly of fibers 107 and 108 will assume the shape shown in FIG. 10-b. As shown in FIG. 10-b, fiber 108, having undergone lower longitudinal shrinkage than fiber 107, forms a curved path 112 which may be approximated by straight lines 113 and 114, forming an aspect angle (a) as shown in FIG. 10-b. For a difference in longitudinal stress-free shrinkage of only 5%, a simple calculation yields an approximated aspect angle (a) of 18 degrees and height 115, [not shown in FIG. 10-b], of formed cell equal to [(tangent of 18 degrees× the shrunk length of high shrinkage fiber 107)/2]. For the typical case of a 2 denier polyester fiber having a diameter of 0.000564 inch, an aspect angle (a) of 18 degrees and a distance between bonding points of 0.1 inch, the open cell has a theoretically calculated maximum pore size equal to (0.32× 0.1×0.5)=0.016 inch which is (0.016/0.000564)=28.3 times the diameter of the fiber. Such an open pore permits flow of air-scenting liquid without any clogging that may be caused by solids left on the surface of the fibers after the solvent or water content of the air-scenting liquid evaporates.

In an actual embodiment of the present invention, a non-clogging porous resilient bonded fibrous foam/mass was made of an intimate blend of two groups of staple fibers. The first group of staple fibers is bicomponent polyester fibers having a sheath material made of low melting point polyester with a melting point of 110 degrees Celsius and a core made of regular polyester with a melting point of 260 degrees Celsius and has i) a percent weight $W1=50$ (%) of the weight of said fibrous mass, ii) an average fiber denier $D1=2$ denier, iii) a ratio $N1$ where $N1$ is equal to $W1/D1=50/2=25$, iv) a staple length $L1=2$ inch, v) a tack point $T1=95$ degrees Celsius and vi) a percentage longitudinal stress-free shrinkage $S1$ (%)=24.4% at said tack point T1. The second group of staple fibers has i) a percent weight $W2$ (%)=50% of the weight of said fibrous mass, ii) an average fiber denier $D2=4$, iii) a ratio $N2$ where $N2$ is equal to $W2/D2=50/4=12.5$, iv) a staple length $L2$, of approximately 2 inches v) a tack point $T2$ of approximately 240 degrees Celsius, vi) a percentage longitudinal stress-free shrinkage $S2$ (%)=1.47% at said tack point T1, and a ratio $R$ equal to $N1/N2=25/12.5=2$. For this intimately blended fibrous mass/foam, the percentage longitudinal stress-free shrinkage difference $SD$ (%)=24.4−1.47=22.93%. The above intimately blended fibrous mass was fed, in the form of slivers weighing 4 gram per yard, into a die, as described above. The die heating zone was fed with steam at nearly atmospheric pressure and a temperature of 212 degrees Fahrenheit. The bonded slivers were formed into a tube having an outer diameter of 1.53 inch and an inner diameter of 0.5 inch and a dry density DD of 0.165 gram per cubic centimeter and used as a wick. One end of the wick (of length 4 inches) was dipped into a bath containing 4 ounces of water-base ink. After 16 days of nearly linear evaporation rate, the entire 4 ounces of water-base ink were wicked through the wick and evaporated leaving a high concentration of ink solids at the top end of the wick. This indicates that such a non-clogging nature of the bonded porous fibrous foam of the present invention is a result of the choice of fibers for making the intimately blended fibrous mass in accordance with the criteria and within the ranges described and detailed above.

The non-clogging resilient porous bonded fibrous foam/mass made in accordance with the teachings of the present invention is also suited for use as an ink reservoir for ink jet printer cartridges.

In accordance with the present invention, the fibrous mass serves the function of being a high capacity reservoir for holding the air-scenting liquid mass, by capillary action, within its pores. Segments of the exterior surface of the fibrous mass, having at least one of the above-mentioned five (5) characteristics, draw the air-scenting liquid from the reservoir (the body of the fibrous mass) to the surface of the fibrous mass and allow it to evaporate at an unexpectedly nearly linear/constant rate the magnitude of which is controlled by allowing evaporation of the air-scenting liquid from predetermined uncovered portion(s) of said segments of the exterior surface of said fibrous mass. To prevent dripping, spillage and leakage of the air-scenting liquid from the device of the present invention, the mass of the air-scenting liquid contained within the body of the fibrous mass (reservoir) is not exceeding, and preferably is less than, the Dripping Liquid Mass (DML) of the extent L of the fibrous mass. The air-scenting device of the present invention also features a long duration of air-scenting at a nearly linear/constant rate of evaporation of the air-scenting liquid. This unexpected feature (the nearly linear rate of evaporation) was found to be possible only when the fibers used for making the porous fibrous mass are non-reactive with and non-absorbent of (i.e., inert to) the air-scenting liquid held within the pores of the bonded porous fibrous mass.

Also, the combination of i) use of non-absorbent and non-reactive fibers for making the bonded porous fibrous mass, ii) said fibers being made of a polymeric material having a density in the range of 1.1 to 1.4 gram per cubic centimeter, iii) said fibers having a denier in the range of 0.9 to 15 denier and preferably in the range of 0.9 to 6 denier, and iv) said fibrous mass having a dry density in the range of 0.1 to 0.45 gram per cubic centimeter yielded the significant and unexpected result of the device non-clogging throughout its long duration performance (air-scenting) period. The unexpected non-clogging performance of the device of the present invention is an indication that the open pores/open cells/open capillaries, of the bonded porous fibrous mass, remain open throughout the entire long-duration performance of the device.

DEFINITIONS

In accordance with the present invention, the following terms are defined as follows:

1) "Free-to-flow liquid mass" is an initially motionless liquid mass or body i) having a planar top surface, said surface being perpendicular to the direction of the gravitational acceleration force, (e.g., as indicated by arrow g in FIGS. 1 and 2), and ii) being contained in a container or placed on top of an impermeable surface whereby upon tilting said container or said impermeable surface the liquid mass may be poured out of the container or flow onto the impermeable surface. Accordingly, liquids 3 in FIGS. 1 and 24 in FIG. 2 are free-to-flow liquid masses.

2) "Porous mass" is a mass or a body having or containing open cells/pores/interstices and permitting the flow of gas or liquid through its pores, open cells or interstices upon the application of a pressure or a force difference between two spaced-apart points in or on the mass.

3) "Fibrous mass" is a mass or a body made of fibers.

4) "Surface Segment of a Mass" is a skin layer of the mass having a thickness within the range of 0.25 to 1.0 millimeter.

5) "Mass Density of a Fibrous Mass or a Surface Segment" is the mass per unit volume of the fibrous mass or the surface segment.

6) "Fiber Orientation Index (FOI) Relative to an Axis or a Direction" is the quotient of (the summation of the number of fibers×their respective angle of orientation, measured in degrees from a specified axis or direction) divided by the total number of fibers. For example, a mass of fibers composed of 50 fibers oriented at an angle of 5 degrees relative to an axis, 30 fibers oriented at angle of 30 degrees relative to the same axis and 20 fibers oriented at an angle of 20 degrees relative to the same axis, has a Fiber Orientation Index FOI relative to the axis=$[(50\times5)+(30\times30)+(20\times20)]/(50+30+20)=15.5$ Degrees.

7) "Extent of an object, a body or a mass" is the longest distance between two points located on the surface of the object, body or mass. For example, the extent of a rectangular block of 3 inch thickness×4 inch width×5 inch length is the distance between the farthermost corners, which is 7.071 inch.

8) "Dry fibrous mass" is a fibrous mass containing no liquids, whether said liquids are i) contained within the fibers (i.e., absorbed by the fibers) and/or ii) held in the pores or spaces between the fibers.

9) "Average Fiber Denier of a Fibrous Mass or a Surface Segment" is the quotient of 100 divided by (the summation of the weight percent of each fiber denier contained in the fibrous mass or surface segment divided by its respective fiber denier). For example, a fibrous mass or surface segment composed of 30% (by weight) of 3 denier fiber, 20% (by weight) of 2 denier fiber and 50% (by weight) of 5 denier fiber has an average fiber denier of $(100/[(30/3)+(20/2)+(50/5)])=100/[10+10+10]=100/30=3.33$ denier.

10) "Capillary pressure or Capillary Rise" is the highest level, vertically measured from the top surface of a liquid, reached by the liquid through a porous or a fibrous body or mass as a result of dipping a portion of the porous or fibrous body or mass into the liquid and allowing wicking action to take place until the liquid rise, above the surface of the liquid and through the porous or fibrous body or mass, reaches an equilibrium point (i.e., the point at which the liquid ceases to rise).

11) "Bonded fibrous mass" is a mass of fibers having at least a portion of its fibers attached, to each other at their contact and/or crossover points and thereby rendering the mass to act as a coherent body which may be handled or moved as a whole even when only a portion of the fibrous mass is moved. The fibers may be attached at their contact and/or crossover points cohesively or by using an adhesive. Cohesively attached fibers are attached to each other by a melting action occurring at the fiber surfaces at said contact and/or crossover points and co-solidification of the melted fiber surfaces upon cooling the fibers. In accordance with the present invention, adhesives used for bonding fibers in a bonded fibrous mass are of a non-absorbent and non-reactive nature to the air-scenting liquid held within the bonded fibrous mass and used for air-scenting.

12) "Liquid Volume Ratio" is the ratio of the volume of the air-scenting liquid held within the pores/capillaries/open cells of the porous fibrous mass to the total volume of the porous fibrous mass. For example a bonded porous fibrous mass in the form of a 1 inch×1 inch×1 inch cube containing 0.60 cubic inches of air-scenting liquid within its pores, has a fluid volume ratio of 0.6 or 60%.

13) "Dripping Liquid Mass of an Extent of a Bonded Porous Fibrous Mass (DML)" is the maximum mass of a liquid withheld entirely within the pores/capillaries/open cells of a bonded porous fibrous mass after initially soaking completely the fibrous mass in a pool of the liquid, removing it from the liquid pool and allowing it to drip, with its extent oriented parallel to the direction of gravitational force, until dripping ceases, i.e., equilibrium is reached and no dripping occurs.

14) "Fibrous Foam" is a network of interconnected fibers having bonds (adhesive and/or cohesive) between fibers having common contact points and joining said fibers at said common contact points and open spaces/pores/cells separating said fibers when the network of fibers is subjected to no externally-applied loading (tensile, compressive and/or shear forces), bending action/moment or torsional/twisting moment/torque. As such, a fibrous foam not subjected to any externally-applied load, bending action and/or twisting moment has a packing factor of less than 0.91 which is the maximum possible packing factor for the case of a fibrous mass made of circular cross-section fibers. The non-clogging resilient porous bonded fibrous foam/mass of the present invention has a packing factor within the range of 0.07 to 0.32.

15) "Packing Factor of a Fibrous Foam/Mass" is the ratio of the volume occupied by the fibers to the total external volume enveloping the fibrous foam/mass.

16) "Resilient Fibrous Foam/Mass" is a fibrous foam/mass, as defined above, which recovers —from a 30% lateral compressive deformation/strain imposed on the foam/mass and maintained for a period of one (1) minute- to at least 95% of its original (pre-deformation) dimensions within a period of one (1) minute from removal of said lateral compressive strain, i.e., has an unrecovered lateral deformation/strain of 5% or less.

17) "Intimately Blended Fibrous Mass" is a fibrous mass comprising at least two different types of fibers dispersed uniformly and randomly throughout the mass such that the probability of finding a particular type fiber at any location, within the fibrous mass, does not vary substantially from one location to another location.

18) "Tack Point or Temperature of a Fiber" is the lowest temperature at which the fiber, upon being folded and pressed against itself or upon being pressed against another object, would stick to itself or to the surface of the object against which it is pressed.

19) "Stress-Free Linear Thermal Shrinkage" is the negative change (final length–initial length) in length per unit length a fiber experiences upon being heated while it is placed on a horizontal surface and allowed to shrink under no external constraints. Expressed as a positive percentage, it is equal to [(Initial Fiber Length Before Heating–Final Fiber Length After Stress-Free Thermal Shrinkage Occurs)/(Initial Fiber Length Before Heating)]×(100).

BRIEF DESCRIPTION OF THE DRAWING

FIG. 1 shows an air-scenting device of the prior art.
FIG. 2 shows an air scenting device of the prior art.
FIG. 3 shows an isometric view of an embodiment of the device of the present invention.
FIG. 4 shows a longitudinal cross-sectional view of a container-type device of the present invention.
FIG. 5 shows a flat configuration of the device of the present invention.
FIG. 6 shows a cross-sectional view of the device shown in FIG. 5.
FIG. 7 shows an elongated (air-scenting reed) type of the device of the present invention.
FIG. 8 shows a cross-sectional view of a circular composite embodiment of the non-clogging fibrous foam of the present invention.
FIG. 9 shows a cross-sectional view of a flat composite embodiment of the non-clogging fibrous foam of the present invention.
FIG. 10 shows a representation of the non-clogging bonded fibrous foam/mass of the present invention.
FIG. 10-a shows two fibers, initially straight and of equal length, bonded together at two points.
FIG. 10-b shows the fibers shown in FIG. 10-a after being heated and forming open cell/spacing between the fibers.
FIG. 11 shows a longitudinal cross-sectional view of another embodiment of the present invention.

BACKGROUND OF THE INVENTION

FIG. 1 shows an air-scenting device 1 of the Prior Art. As shown therein, it comprises a container or bottle 2 made of glass, non-reactive and non-absorbent plastics or metal. Container 2 is filled, at least partially, with a free-to-flow liquid mass 3 of an air-scenting liquid which may be a water-base, oil-base and/or solvent-base liquid. A wick 4 is placed into container 2, usually in a substantially vertical orientation, and is partially immersed into liquid mass 3. Wick 4 is usually guided/surrounded by a guide/spacer 5 through the neck 9 of container 2. An air pressure equalization vent or hole 6 is provided in order to maintain the same air pressure inside of and outside of container 2. A cap 7 is used for covering the top portion of wick 4 and sealing container 2 at sealing closure 8. Upon removing cap 7, the air-scenting liquid, contained within the pores of wick 4, evaporates into the ambient air and scents the ambient air accordingly. Optionally, the top portion of wick 4 may be heated in order to accelerate the rate of evaporation of the air-scenting liquid. Also, optionally, a fan-type air blower is used for the same purpose of increasing the rate of evaporation of the air-scenting liquid.

Because of sealing closure 8, no leakage or spillage occurs while transporting air-scenting device 1 and prior to removing cap 7. On the other hand, some liquid may accumulate in space 10 between cap 7 and wick 4 which might contact the hand of the user of device 1 or drip on the floor upon removing cap 7. Since a majority of air-scenting liquids have skin and/or eye irritating effects, extra care must be exercised by the user of device 1. Also, a dripping/dripped liquid, especially on a tile floor, may present a slipping and falling hazard to persons stepping on it or walking on it.

The air-scenting device of the present invention overcomes the above mentioned drawbacks of prior art air-scenting devices by containing no free-to-flow air-scenting liquid mass. Another drawback of the prior art air-scenting devices, which are designed to operate similarly, is that they can perform only in a substantially vertical orientation with the free-to-flow air-scenting liquid mass at the bottom of container 4. Also, when turned upside down, device 1 tends to drip liquid 3, through vent 6, when the ambient temperature rises. The air-scenting device of the present invention overcomes these drawbacks and does not drip or leak any air-scenting liquid regardless of its orientation relative to the direction of the gravitational acceleration force.

FIG. 2 shows another air-scenting device 20 of the prior art. As shown therein, it comprises an initially sealed container 21 having a container lid 22 and a thin pierceable (i.e., may be pierced) membrane 23. Container 21 contains free-to-flow air-scenting liquid mass 24. As shown in FIG. 2, an air gap 21a exists between the planar top surface of liquid mass 24 and lid 22. Container 21 is surrounded with a wick 25, usually in the form of a sleeve which may be made of a fibrous material such as paper or a textile material or a sintered plastics particles. As shown in FIG. 2, the assembly of container 21 and wick 25 are placed into external cup 26. Cup 26 has a trough or basin 27 which is impermeable and has a height 29, as shown in FIG. 2, and membrane piercing tip 26a and an aperture zone 28. Upon pushing membrane 23 against tip 26a and thereby piercing membrane 23 liquid 24 flows out of container 21 into basin 27 and rises to level 29a which, by design, is lower than height 29. As a result of liquid 24 flowing out of container 21 into basin 27 the air pressure in air bubble 21a becomes lower than the surrounding atmospheric pressure and flow of liquid 24 stops. As air-scenting liquid gets absorbed by wick 25, it evaporates into the ambient air and scents the surrounding air. Also, as the level of air scenting liquid in basin 27 gets lower, due to continuous wicking and evaporation, a certain low level 29b is reached where, similar to what occurs in a bottle-type water bubbler, an air bubble escapes through punctured membrane 23 into the interior of container 21 in order to re-establish a new pressure equilibrium between the interior of container 21 and the surrounding atmospheric pressure. Similar to device 1, shown in FIG. 1, air scenting may, optionally be accelerated by the use of a fan-type blower.

Some of the drawbacks of air-scenting devices of the type shown in FIG. 2 are that spillage occurs when the device is tilted and therefore, these devices must be kept vertically oriented once membrane 23 is pierced. Also, when the ambient temperature increases, the air pressure in air space 21a increases and additional liquid flows from container 21 into basin 27, overflows beyond level 29, and drips below the entire device.

The above description of prior art air-scenting devices is hereby incorporated in this present invention disclosure for the purpose of incorporating portions of it in future Continuation-in-Part patent applications and/or in future amendments of claims.

The air-scenting device of the present invention overcomes all of the above-mentioned drawbacks while providing a long lasting duration of scenting the ambient air at a nearly linear rate of releasing air freshening liquid into the surrounding environment.

DETAILED DESCRIPTION OF THE INVENTION

Device

FIG. 3 shows an embodiment of the device of the present invention. As shown therein, non-dripping and spillage and leakage-proof air-scenting device 30, comprises the following elements/components which are described and arranged relative to each other as follows:

A) An initially-dry porous bonded fibrous mass 31, having an initial dry mass MID, a volume V and an extent L, as shown in FIG. 3. Fibrous mass 31 has a dry density DD=(MD)/(V). Dry density DD may be within the range of 0.08 to 0.9 gram per cubic centimeter. A preferred range of dry density DD is within the range of 0.10 to 0.45 gram per cubic centimeter. In accordance with the present invention, fibrous mass 31 is non-reactive to and non-absorbent of the air-scenting liquid that is or that will be used for scenting the surrounding atmosphere. This is assured by selecting non-absorbent and non-reactive fibers (i.e., fibers that are non-absorbent of and inert to the air-scenting liquid that is or that will be used for scenting the surrounding atmosphere) for making fibrous mass 31. Examples of such fibers are polypropylene, polyethylene, nylon and polyester fibers. As a result, and in accordance with the present invention, the air-scenting liquid mass is retained/held substantially entirely within the capillaries/open cells/interstices/pores of body 32 of fibrous mass 31 and in a squeezable liquid-phase. A squeezable liquid-phase means that the air-scenting liquid may be extracted, from the fibrous mass, by applying a squeezing action, on the fibrous mass, which is sufficient for extracting the air-scenting liquid, at least in droplet form, without resulting in disintegration of the fibrous mass holding the air-scenting liquid.

As compared to non-dripping prior art air-scenting devices, (for example parchment-type paper air-scenting devices used for scenting the interior of cars and trucks), the air-scenting device of the present invention retains the air-scenting liquid, stored in fibrous mass 31, in a squeezable liquid-phase held substantially entirely within the open cells/pores of body 32 of fibrous mass 31.

In accordance with the present invention, fibrous mass 31 is impregnated with a non-reactive air-scenting liquid (not shown) having a mass MF where MF is not exceeding the Dripping Liquid Mass (DML) of the specific combination of i) extent L of body 32, ii) dry density DD of fibrous mass 31, iii) the specifications and types of fibers from which fibrous mass 31 is made and iv) the selected air-scenting liquid. Accordingly, membrane, coating, enclosure or container 35, shown in FIG. 3, contains no free-to-flow air-scenting liquid and the air-scenting liquid held within fibrous mass 31 is retained only in a squeezable liquid-phase and is held entirely within the open cells/capillaries of body 32 of fibrous mass 31 without dripping under the action of the gravitational force and regardless of the orientation of fibrous mass 31 or device 30 relative to the direction of the gravitational force, thereby making air-scenting device 30 non-dripping and spillage and leakage-proof.

The fibers comprising fibrous mass 31 are bonded to each other, either cohesively or using an adhesive that is non-reactive to and non-absorbent of (i.e., inert to) the air-scenting liquid that is stored in body 32 of fibrous mass 31. An example of a non-reactive adhesive is water-base polyurethane adhesive which is readily available from a variety of suppliers. Fibrous mass 31 may be in any solid (three-dimensional) form or shape, including flat, cylindrical, prism, spherical, cubical, hollow or any other three dimensional shape, including profile-cut, embossed and sculptured shapes.

In accordance with the present invention, body 32, (as impregnated with a mass MF of air-scenting liquid, where MF, as described earlier, is not exceeding Dripping Liquid Mass (DML)), of fibrous mass 31 serves the function of being a high capacity reservoir for holding, in a squeezable liquid-phase, the air-scenting liquid.

In an embodiment of the present invention, fibrous mass 31 is made of polyester fibers. Generally speaking, polyester fibers are inert to most water-base, solvent-base and oil air-scenting liquids. In accordance with the present invention the denier of fibers used for making fibrous mass 31 is within the range of 0.9 to 15 and preferably in the range of 0.9 to 6 denier. For the same dry density DD of fibrous mass 31, the use of finer fibers, for making fibrous mass 31, usually results in a higher Capillary Rise/Capillary Pressure, higher Liquid Volume Ratio, higher Dripping Liquid Mass (DML) and a greater wicking action.

In accordance with the present invention, a variety of fiber blends may be used for making the feedstock slivers for making cohesively-bonded fibrous mass 31, for example i) slivers weighing 4 gram per yard and made of a blend of bicomponent (Sheath-Core type) 2 denier polyester fibers having a weight of 50% and 4 denier regular polyester fibers having a weight of 50%. The sheath of the bicomponent fibers has a lower melting point than the core and than the regular polyester fibers. The melting point of the sheath of the bicomponent fibers is around 110 degrees Celsius and the melting points of the core of the bicomponent fibers and the regular polyester fibers are much higher, around 260 degrees Celsius. Such bicomponent fibers are readily available from a variety of suppliers and in a variety of deniers and colors, ii) slivers weighing 5 gram per yard and made of a blend of bicomponent (Sheath-Core type, as described above) 2 denier polyester fibers having a weight of 50% and 1.5 denier regular polyester fibers having a weight of 50%, and iii) slivers weighing 5 gram per yard and made of a blend of bicomponent (Sheath-Core type, as described above) 2 denier polyester fibers having a weight of 75 to 80% and 1.5 denier regular polyester fibers having a weight of 20 to 25%. An advantage of using a fiber blend with a higher %, by weight, of such bicomponent fibers is that the resulting bonded fibrous mass has higher rigidity and therefore is easier to handle in subsequent processes. The slivers used as feedstock material for making bonded fibrous mass 31 may be made on cotton/synthetic fiber cards or on woolen or worsted cards. Cotton/synthetic fiber cards are preferred though their use is usually limited to a relatively shorter staple fiber length, for example around 2 inches.

Other non-absorbent and non-reactive fibers, including regular and bicomponent type fibers may also be used, for example similar blends of regular and bicomponemt polypropylene fibers.

In a preferred embodiment of the present invention, polyester fibers in the form of slivers (weighing 4 gram per yard and made of a blend of bicomponent (Sheath-Core type, as described above) 2 denier polyester fibers having a weight of 50% and 4 denier regular polyester fibers having a weight of 50% were used for making a tubular porous bonded fibrous mass having an outer diameter of 1.53 inch, an inner diameter of 0.5 inch, a length of 4 inch, an Extent L of 4.283 inch a dry mass (MD) of 17.8 gram and a dry density (DD) of 0.165 gram/cc. The bonded porous fibrous mass had a water and alcohol-base air scenting Dripping Liquid Mass of 90.1 gram and a saturated non-dripping weight/mass of 107.9 gram and a saturated non-dripping density of 1.0024 gram/cc. The saturated non-dripping weight/mass is defined as the summation of the dry mass of the fibrous mass plus the Dripping Liquid Mass (DML). The saturated non-dripping density is defined as the saturated non-dripping mass divided by the volume of the bonded fibrous mass. An analysis of the above data yields a Liquid Volume Ratio of 83.7%. This is an unexpected and unusually high Liquid Volume Ratio, especially as compared to air-scenting devices that utilize sintered plastic particles for holding the air-scenting liquid and or for wicking.

In another embodiment of the present invention, polyester fibers in the form of slivers (weighing 5 gram per yard and made of a blend of bicomponent (Sheath-Core type, as described above) 2 denier polyester fibers having a weight of 75% and 1.5 denier regular polyester fibers having a weight of 25% were used for making a cylindrical porous bonded fibrous mass having an outer diameter of 3.00 inch, a length of 4.75 inch, an Extent L of 5.62 inch a dry mass (MD) of 92.0 gram and a dry density (DD) of 0.167 gram/cc. The bonded porous fibrous mass had a water and alcohol-base air scenting Dripping Liquid Mass of 309.7 gram and a saturated non-dripping weight of 401.7 gram and a saturated non-dripping density of 0.730 gram/cc. The saturated non-dripping mass is defined as the summation of the dry mass of the fibrous mass plus the Dripping Liquid Mass (DML). The saturated non-dripping density is defined as the saturated non-dripping mass divided by the volume of the bonded fibrous mass. An analysis of the above data yields a Liquid Volume Ratio of 56.28%.

In yet another relatively high dry density embodiment of fibrous mass 31 of the present invention, polyester fibers in the form of slivers (weighing 4 gram per yard and made of a blend of bicomponent (Sheath-Core type, as described above) 4 denier polyester fibers having a weight of 50% and 4 denier regular polyester fibers having a weight of 50% were used for making a rectangular cross-section (0.307 inch×0.357 inch) porous bonded fibrous mass having a length of 7.02 inch, an Extent L of 7.036 inch, a dry mass (MD) of 6.178 gram and a dry density (DD) of 0.49 gram/cc. The bonded porous fibrous mass had a water and alcohol-base air scenting Dripping Liquid Mass of 5.202 gram and a saturated non-dripping weight of 11.4 gram and a saturated non-dripping density of 0.90 gram/cc. The saturated non-dripping mass is defined as the summation of the dry mass of the fibrous mass plus the Dripping Liquid Mass (DML). The saturated non-dripping density is defined as the saturated non-dripping mass divided by the volume of the bonded fibrous mass. An analysis of the above data yields a Liquid Volume Ratio of 41.4%.

Fibrous mass 31 of device 30 may be impregnated with the air-scenting liquid by injection, soaking, dipping or spraying.

Polyester fibers, being non-reactive to and non-absorbent of most air-scenting liquids, are particularly preferred for making fibrous mass 31 since their use offers the following advantages; i) making the device of the present invention useful for water-base, alcohol-base, solvent-base and oil air-scenting liquids without absorption of and/or reaction with the fibers of the porous fibrous mass 31 and ii) increasing/maximizing the Dripping Liquid Mass (DML), the Liquid Volume Ratio and the air-scenting liquid holding capacity of the porous fibrous mass 31, as compared to devices having the same dry density but made of fibers having lower density, such as polypropylene. (Density of polypropylene=0.91 gram/cc and density of Polyester=1.38 gram/cc).

In a process for making bonded fibrous mass 31, feedstock slivers of staple polyester fibers (for example in blends as described above) are fed into a heat bonding (cohesive bonding) die. The bonding die has a feed/inlet zone, a heating zone, a tapered compaction zone and a shaping/cross-section-forming zone for making/shaping the final cross sectional shape of the bonded fibrous mass. The compaction zone is preferably tapered at an angle of 10 degrees to 45 degrees, per side, relative to the axis of the die in order to provide more effective contact and higher heat transfer rate from the die body to the feedstock slivers thus effecting a calendaring or glazing action that renders the exterior surface, of the bonded fibrous mass, having higher capillary rise and/or a higher density than the interior of the fibrous mass. Dragging of the feedstock fibers against the interior surface of the die causes the fibers on the exterior surface of the bonded fibrous mass to have a higher fiber orientation index. In other embodiments, the feedstock slivers or needle punched nonwoven sheets may be arranged in layers which may be parallel flat layers or concentric circles having outer layer(s) made of finer fibers (lower denier). The heating zone of the die is fed and filled with hot steam or hot air at a temperature of approximately 200 to 220 degrees Fahrenheit and the feedstock is pulled through the die. Cohesive bonding between the fibers occurs inside the die. The pulled bonded fibrous mass is subsequently cut to a desired length.

Alternatively, the fibrous feedstock is adhesively bonded by dipping it into an adhesive bath, feeding it through a squeezing die and subsequently into a shaping die and curing the adhesive. This process is also known in the art as Pultrusion.

Optionally, the surface of fibrous mass 31 is treated/coated with a surfactant. An example of a surfactant that may be used for coating the exterior surface of fibrous mass 31 is sold by Sybron Chemicals, Inc, under the Tradename of TANAWET RCN. Other surfactants are readily available from other suppliers. In some applications of the present invention, the entire fibrous mass may be soaked into a 1% concentration surfactant in order to enhance the wicking rate of the air-scenting liquid contained inside the fibrous mass.

Fibrous mass 31 has a body 32 and an exterior surface 33. Body 32 has a capillary pressure BCP, a mass density MDB, an average fiber denier FDB, and a fiber orientation index FOIB relative to an axis or a direction. The exterior surface 33 comprises surface segments 34. Surface segments 34 have at least one of i) a capillary pressure SCP, where SCP is higher than said capillary pressure BCP, ii) a mass density of MDSG (gram/cubic centimeter) where MDSG is higher than said mass density MDB, iii) an average fiber denier FDSG where FDSG is lower than said FDB, iv) fiber orientation/alignment index FOISG where FOISG is higher than said FOIB as measured relative to said axis or direction, and v) a surfactant coating applied to said surface segments.

B) As shown in FIG. 3, portion(s) 36 of surface segment(s) 34 are covered with or contained in a liquid-impermeable membrane, coating, enclosure or container 35. Membrane, coating, enclosure or container 35 is made of a material which is non-reactive to and non-absorbent of the air-scenting liquid used for impregnating fibrous mass 31. The mass of air-scenting liquid (MF) impregnated into fibrous mass 31 is not exceeding the Dripping Liquid Mass (MDL) of the specific combination of i) extent L of body 32, ii) dry density DD of fibrous mass 31, iii) the specifications and types of fibers from which fibrous mass 31 is made and iv) the selected air-scenting liquid. Additionally, and in accordance with the present invention, liquid-impermeable membrane, enclosure or container 35 contains no free-to-flow liquid mass.

Membrane, coating, enclosure or container 35 is adapted to cover predetermined portion(s) 36 of surface segment(s) 34 and to allow certain remaining segment(s) 37 to be uncovered or to remain uncovered, thereby i) allowing a predetermined rate of evaporation of the air-scenting liquid-upon impregnating fibrous mass 31 with said air-scenting liquid and exposing/uncovering said remaining portion(s) 37 of said surface segment(s) 34 to surrounding atmosphere- to occur through said remaining portion(s) 37 of said surface segment(s) 34 and ii) controlling the rate of release of the air-scenting liquid into the surrounding atmosphere.

Examples of membrane 35, wrapped around the exterior of fibrous mass 31, are polyethylene, polyester and polypropylene films, including heat-shrink-type wrapping films, preferably in a thickness in the range of 0.001 inch to 0.006 inch. Membrane 35 may also have surface discontinuities such as perforations, microperforations, or slits or have no surface discontinuities. Membrane 35 may be wrapped around fibrous mass 31 and heat sealed to itself and/or onto fibrous mass 31, stapled into fibrous mass 31, or ultrasonically sealed to itself and/or attached to fibrous mass 31. Alternatively, an example of coating 35 is a water-base polyurethane coating which is self curing and may be partially applied onto the surface of fibrous mass 31 by brushing, spraying, quick dipping or other methods. Also, alternatively, container or enclosure 35 may be made of plastics materials, non-corroding metals or glass.

As such, the combination of impregnated fibrous mass 31, as described above, and membrane, coating, enclosure or container 35, as described above, constitute the device of the present invention which features the following novel and distinguishing combination:

1) Absence of any free-to-flow air-scenting liquid in the entire device and therefore a non-dripping and spillage and leakage-proof air-scenting device and method, regardless of the orientation of the device. This is made possible by impregnating fibrous mass 31 with a mass (MF) of air-scenting liquid where (MF) is not exceeding the Dripping Liquid Mass (DML) of the specific combination of i) extent L of body 32, ii) dry density DD of fibrous mass 31, iii) the specifications and types of fibers from which fibrous mass 31 is made and iv) the selected air-scenting liquid, 2) A novel combination of i) low dry density of fibrous mass 31, preferably within the range of 0.1 to 0.45 gram/cc, and ii) use of fine (low denier) fibers, preferably within the range of 0.9 to 6 denier, made from materials having density within the range of 1.1 to 1.4 gram/cc, thus resulting in body 32, of fibrous mass 31, having a high Liquid Volume Ratio that enables it (body 32) to function as a high capacity reservoir of air-scenting liquid and therefore long lasting/long duration of operation of device 30. In a preferred embodiment of the device of the present invention the Liquid Volume Ratio is in the range of 40% to 87%.

3) Large open cells/pores/capillaries and therefore non-clogging performance throughout the duration of operation of the device. Such large open cells and non-clogging performance of device 31 are another result of the novel combination of i) low dry density of fibrous mass 31, preferably within the range of 0.1 to 0.45 gram/cc, ii) use of fine (low denier) fibers, preferably within the range of 0.9 to 6 denier, made from materials having density within the range of 1.1 to 1.4 gram/cc and iii) a high Liquid Volume Ratio of body 32 of fibrous mass 31, 4) Controllable rate of release of air-scenting liquid, by allowing release and evaporation of the air-scenting liquid from pre-determined exposed or adapted to be exposed surface segments, 5) Nearly linear rate of release of the air-scenting liquid, and
6) Availability in any solid (three-dimensional) form or shape, including flat, cylindrical, prism, spherical, cubical, hollow or any other three dimensional shape, including profile-cut, embossed and sculptured shapes.

FIG. 4 shows another embodiment 40 of the air-scenting device of the present invention. As shown therein, air scenting device 40 comprises an initially dry non-clogging porous bonded fibrous mass 41, made in accordance with the teachings of the present invention, in the form of a cylinder having surface segments 41-*a*. In comparison to the body (interior) of bonded fibrous mass 41, surface segments 41-*a* have at least one of i) higher capillary pressure, ii) higher mass density, iii) lower average fiber denier, iv) higher fiber orientation index relative to the axis of the cylinder and v) a surfactant coating. As shown in FIG. 4, fibrous mass 41 is partially wrapped with impermeable membrane 42 which covers a portion of its exterior surface and leaves an uncovered portion 41-*b*. As desired and as a means for controlling the rate of evaporation of the air scenting liquid from device 40, the area of uncovered portion 41-*b*, of the exterior surface of fibrous mass 41, may be increased or decreased. Alternatively and/or additionally impermeable membrane 42 may be perforated as desired in order to allow evaporation of the air-scenting liquid through the perforated areas or holes. Bonded fibrous mass 41 is impregnated with an air-scenting liquid mass not exceeding the Dripping Liquid Mass (DML) of the extent of bonded porous fibrous mass 41. Fibrous mass 41 is held by holder 44. Holder 44 may take a variety of shapes, forms and dimensions. As shown in FIG. 4, holder 44 is in the form of a bottle cap having a threaded interior to engage with the threaded top of external container 49. Holder 44 is also adapted to have projection 45 which engages with the top end of cylindrical pin 43-*a* of encapsulating member 43, thereby encapsulating bonded fibrous mass 41. Prior to use, cap 44 and external container 49 provide a sealed containment means for air-scenting liquid-impregnated body 41. To use device 40 for air-scenting, container 49 is removed and cap 44, acting as a holder of body 41 is suspended in the space to be air-scented. A variety of means are possible for suspending device 40. As shown in FIG. 4, cap 44 is adapted to have a peripheral extension 46 with at least one hole 47 adapted to receive hook 48 anchored to surface, wall, or device enclosure body 48-*b*. To avoid contacting the air-scenting liquid contained within body 41, device 41, as received, i.e., with container 49 fully engaged with cap 44, is first suspended by engaging hook 48 into hole 47 of extension 46. Next, the user of device 40 swings device 40 in direction of arrow R, shown in FIG. 4, untwists, slides and removes away container 49 and allows the device to swing back to its intended orientation. Alternatively, holding cap 44 may be adapted with two parallel non-conductive electric outlet-type prongs (46-*b*) which may be inserted in a standard electric outlet. Also alternatively, holder 44 may be adapted to have a hook 46-*a* which may be used for suspending device 40 from rod or pin 48-*a*.

FIG. 5 shows a flat embodiment of the device of the present invention. As shown therein and in FIG. 6, (which is a cross-sectional view Q-Q), device 50 comprises non-clogging bonded porous fibrous mass 51 which is impregnated with a mass of air-scenting liquid not exceeding the dripping liquid mass of its extent. As compared to the interior of body 51, outer surface segments 51-*a* have at least one of i) higher capillary pressure, higher mass density, iii) lower average fiber denier, iv) higher fiber orientation index relative to the axis of device 50 and v) a surfactant coating. Impregnated bonded fibrous mass 51 is enclosed between two layers of impermeable membranes 52 which are sealed around their perimeter in order to provide a sealed enclosure for air-scenting liquid-impregnated fibrous mass 51. At least one side of impermeable membranes 52 has at least one opening/aperture 54 which is initially covered by removable/peelable impermeable linear 53. Membranes 52 may be adapted to have an extension 56 and a hook 56-*a* for adapting device 50 for suspension onto pin or rod 58. To use air-scenting device 50, the user holds tab 57 and peels liner 54 thereby allowing the evaporation of the air-scenting liquid through aperture 53.

FIG. 7 shows another embodiment of the device of the present invention in the form of an air-scenting reed 70. As shown therein, reed 70 comprises a non-clogging porous bonded fibrous mass 71 which is partially covered by impermeable membrane 72. As compared to interior of body of fibrous mass 71, outer surface segments 71-*a* have at least one of i) higher capillary pressure, ii) higher mass density, iii) lower average fiber denier, iv) higher fiber orientation index relative to the axis of the reed and v) a surfactant coating. Additionally, to increase the rate of evaporation of the air-scenting liquid contained within the pores of bonded fibrous mass 71, membrane 72 may also have perforations 73 at locations as desired or preferred. The end of reed 70 may be cut in a plane A perpendicular to its axis, as shown in FIG. 7 where angle q is 90 degrees. Alternatively, a beveled cut may be desirable for which angle q may be larger than or smaller than 90 degrees.

FIGS. 8 and 9 show cross-sectional views of alternative constructions of the non-clogging bonded porous fibrous mass. FIG. 8 shows a cross section of a cylindrical configuration porous bonded fibrous mass 71 comprising an external bonded porous fibrous region 71-*a* and a core/interior bonded fibrous region 71-*b*. In accordance with the present invention, fibrous regions 71-*a* and 71-*b* may have different capillary pressures, mass densities, average fiber deniers, fiber orientation indexes and/or surface coatings.

Similarly, as shown in FIG. 9, flat configuration porous bonded fibrous mass 51 comprising an external bonded porous fibrous regions 51-*a* and interior bonded fibrous region 51-*b*. In accordance with the present invention, fibrous regions 51-*a* and 51-*b* may have different capillary pressures, mass densities, average fiber deniers, fiber orientation indexes and/or surface coatings.

FIG. 11 shows a longitudinal cross-sectional view of another embodiment of the present invention. As shown therein, Device 120 comprises the following components which are described and arranged relative to each other as follows:

An initially-dry porous bonded fibrous mass 121, having an initial dry mass MD, a volume V and an extent L, as shown in FIG. 11. Fibrous mass 121 has a dry density DD=(MD)/(V). Dry density DD, of fibrous mass 121, may be within the range of 0.08 to 0.9 gram per cubic centimeter. A preferred range of dry density DD is within the range of 0.10 to 0.45 gram per cubic centimeter. Fibrous mass 121 is non-reactive to and non-absorbent of the air-scenting liquid that is used for scenting the surrounding atmosphere. Fibrous mass 121 is preferably made of Polyester fibers. The air-scenting liquid mass is retained substantially entirely within the capillaries of body 122 of fibrous mass 121 and in a squeezable liquid-phase. A squeezable liquid-phase means that the air-scenting liquid may be extracted, from the fibrous mass, by applying a squeezing action, on the fibrous mass, which is sufficient for extracting the air-scenting liquid at least in droplet form, without resulting in disintegration of the fibrous mass holding the air-scenting liquid.

Fibrous mass 121 is impregnated with a non-reactive air-scenting liquid (not shown) having a mass MF where MF is not exceeding the Dripping Liquid Mass (DML) of the specific combination of i) extent L of body 122, ii) dry density DD of fibrous mass 121, iii) the specifications and types of fibers from which fibrous mass 121 is made and iv) the selected air-scenting liquid. Fibrous mass 121 is partially covered and partially contained within an impermeable container 125, shown in FIG. 11. Device 120 contains no free-to-flow air-scenting liquid and the air-scenting liquid is held within fibrous mass 121 without dripping under the action of the gravitational force (represented by arrow g in FIG. 11) and regardless of the orientation of fibrous mass 121 or device 120 relative to the direction of the gravitational force, thereby making air-scenting device 120 non-dripping and spillage and leakage-proof.

The fibers comprising fibrous mass 121 are cohesively (i.e., adhesive-free) bonded to each other. As shown in FIG. 11, fibrous mass 121 is made of Polyester fibers in the form of a hollow cylinder (for example 1.5" O.D., 0.5" I.D., 3.75" Length).

As shown in FIG. 11, portion 126 of surface 124 of fibrous mass 121 is covered with and contained within liquid-impermeable container 125. Container 125 is made of a material which is non-reactive to and non-absorbent of the air-scenting liquid used for impregnating fibrous mass 121.

Additionally, the assembly of fibrous mass 121 and impermeable container 125 contains no free-to-flow liquid mass.

Container 125 is adapted to cover a predetermined portion 126 of surface 124 and to allow a certain remaining surface segment 127 to be uncovered or to remain uncovered, thereby i) allowing a predetermined rate of evaporation of the air-scenting liquid-upon impregnating fibrous mass 121 with the air-scenting liquid and exposing/uncovering the remaining surface segment 127 of surface 124 to surrounding atmosphere to occur through the remaining portion 127 of surface 124 and ii) controlling the rate of release of the air-scenting liquid into the surrounding atmosphere.

Prior to use, fibrous mass 121, contained within container 125 is covered by an impermeable cap 123. Impermeable cap 123 is adapted to effect a seal between itself and container 125 at contact zone/periphery 129, thus encapsulating fibrous mass 121 and preventing any evaporation of the air-scenting liquid contained within fibrous mass 121. Cap 123 may be adapted to have a projection 130-*a* in order to facilitate twisting and untwisting of cap 123 onto and off container 125. The bottom end 128 of container 125 is adapted to fit into and be held within a wall-suspended dispenser (not shown). For example, and as shown in FIG. 11, bottom end 128 of container 125 has thread 131 adapted to fit into and be held within a wall-suspended enclosure/dispenser having a corresponding threaded opening. Bottom end 128 of container 125 may also be adapted to have projection 130-*b* in order to facilitate twisting and untwisting container 125 into and out of said wall-suspended enclosure/dispenser.

Method

In accordance with the present invention, with reference to FIG. 3 and with reference to and incorporation, by reference and in its entirety, of the above section, titled DEVICE, a non-dripping and spillage and leakage-proof air-scenting method comprises the following steps:

1) Providing an initially-dry porous bonded fibrous mass (31), said fibrous mass having an initial dry mass MD, an extent L and a volume V, said fibrous mass having a body B (32) and an exterior surface S (33), said body having a capillary pressure BCP, a mass density MDB, an average fiber denier FDB, a fiber orientation index FOIB relative to an axis or a direction, said exterior surface S (33) comprising surface segments SG (34), said surface segments SG (34) having at least one of i) a capillary pressure SCP, where SCP is higher than said capillary pressure BCP, ii) a mass density of MDSG (gram/cubic centimeter) where MDSG is higher than said mass density MDB, iii) an average fiber denier FDSG where FDSG is lower than said FDB, iv) fiber orientation/alignment index FOISG where FOISG is higher than said FOIB as measured relative to said axis or direction, and v) a surfactant coating applied to said surface segments SG (34), 2) Covering or containing a portion P (36) of said surface segments SG (34) with a liquid-impermeable membrane or enclosure or within a container E (35), said membrane, enclosure or container containing no free-to-flow liquid mass, and adapting the remaining portion RSG (37), of said surface segments SG (34), to be or to remain uncovered, thereby i) allowing a predetermined rate of evaporation of an air-scenting liquid-upon impregnating said fibrous mass with said air-scenting liquid and exposing/uncovering said remaining portion RSG (37) of said surface segments to surrounding atmosphere- to occur through said remaining portion RSG (37) of said surface segments SG (34) and ii) controlling the rate of release of said air-scenting liquid into said surrounding atmosphere, said fibrous mass and said membrane, enclosure or container E (35) being non-reactive (inert) to and non-absorbent of said air scenting liquid, and 3) Impregnating said fibrous mass with said air-scenting liquid of mass MF where MF is not exceeding the dripping liquid mass DML of said extent L of said body, thus retaining said air-scenting liquid in a squeezable liquid-phase and held entirely within the open cells/pores/capillaries of said body of said fibrous mass without dripping under the action of the gravitational force and regardless of the orientation of said fibrous mass relative to the direction of the gravitational force, thereby making said air-scenting method non-dripping and spillage and leakage-proof.

In accordance with the present invention, a linear rate (or a constant rate) of releasing air freshening/scenting liquid/vapor, means that the rate of release and evaporation of the air-scenting liquid during the period starting after the first 10% of the recommended/design duration of use and ending upon reaching 90% of the recommended duration of use is substantially constant. For example, a nearly linear/constant-rate air scenting device having a nearly linear rate of release of air-scenting liquid and a designed/recommended use period of 30 days has a nearly constant rate of release of air-scenting liquid starting from about the $4^{th}$ day of use through the end of the $27th^{th}$ day of use. Naturally, in actual use, and due to fluctuations in ambient conditions, the rate of release and evaporation of the air-scenting fluid, though characterized as nearly linear, fluctuates within a range of about +/−15% of the average release and evaporation rate of the air-scenting liquid.

The invention claimed is:

1. A non-clogging, non-dripping and spillage and leakage-proof air-scenting device, regardless of its orientation relative to the direction of the gravitational acceleration force, said device allowing a predetermined rate of evaporation of air-scenting liquid, said device comprising: an initially-dry porous bonded fibrous mass, said fibrous mass having an initial dry mass MD, an extent L and a volume V, said fibrous mass having a body B and an exterior surface S, wherein said body having a capillary pressure BCP, a mass density MDB, an average fiber denier FDB, and a fiber orientation index FOIB relative to an axis or a direction, said fibrous mass being impregnated with an air-scenting liquid of mass MF where MF is not exceeding the dripping liquid mass DML of said extent L of said body B, thus i) retaining said air-scenting liquid in a squeezable liquid phase and held entirely within the open cells of said body B of said fibrous mass without dripping, spilling or leaking under the action of the gravitational force and regardless of the orientation of said fibrous mass relative to the direction of the gravitational force, and ii) serving the function of being a reservoir for holding said air-scenting liquid mass MF, by capillary action, within its pores, said exterior surface S comprising surface segments SG, wherein said surface segments SG having at least one of i) a capillary pressure SCP, where SCP is higher than said capillary pressure BCP, ii) a mass density of MDSG (gram/cubic centimeter) where MDSG is higher than said mass density MDB, iii) an average fiber denier FDSG where FDSG is lower than said FDB, iv) a fiber orientation/alignment index FOISG where FOISG is higher than said FOIB as measured relative to said axis or direction, and v) a surfactant coating applied to said surface segments SG, thus drawing said air-scenting liquid from said body of said fibrous mass to the surface of said fibrous mass and allowing said air-scenting liquid to evaporate, said surface segments SG having a portion P, said portion P being covered with a liquid-impermeable membrane or enclosure or contained within a container E, said membrane, enclosure or container containing no free-to-flow liquid mass, and an uncovered remaining portion RSG, thereby i) allowing a predetermined rate of evaporation of said air-scenting liquid to occur through said uncovered remaining portion RSG of said surface segments and ii) controlling the rate of release of said air-scenting liquid into the surrounding atmosphere, said fibrous mass and said membrane, enclosure or container E being non-reactive (inert) to and non-absorbent of said air scenting liquid, said bonded fibrous mass being a flat bonded porous fibrous mass enclosed between two layers of impermeable membranes, said impermeable membranes being sealed around their perimeter, and wherein at least one of said impermeable membranes having at least one opening.

* * * * *